(12) United States Patent
Glänzer

(10) Patent No.: US 7,785,629 B2
(45) Date of Patent: Aug. 31, 2010

(54) BICALUTAMIDE-ADSORBATES, PROCESS FOR PREPARING SAME, AND PHARMACEUTICAL COMPOSITIONS THEREOF

(75) Inventor: Klaus Glänzer, Hamburg (DE)

(73) Assignee: Helm AG, Hamburg (DE)

( * ) Notice: Subject to any disclaimer, the term of this patent is extended or adjusted under 35 U.S.C. 154(b) by 1471 days.

(21) Appl. No.: 11/156,576

(22) Filed: Jun. 21, 2005

(65) Prior Publication Data

US 2006/0286162 A1 Dec. 21, 2006

(51) Int. Cl.
*A61K 9/14* (2006.01)
*A61K 9/50* (2006.01)

(52) U.S. Cl. ........................ 424/489; 424/499
(58) Field of Classification Search .............. None
See application file for complete search history.

(56) References Cited

U.S. PATENT DOCUMENTS 6,436,440 B1 * 8/2002 Meffert et al. .............. 424/486
6,861,557 B2 3/2005 Dolitzky et al. ............. 564/124
2004/0022844 A1 * 2/2004 Hasenzahl et al. .......... 424/452
2005/0033082 A1 2/2005 Bor et al. .................... 558/410

FOREIGN PATENT DOCUMENTS

WO   WO 03/097590        11/2003
WO   WO 2004/100944      11/2004
WO   WO 2004100944 A1 *  11/2004

OTHER PUBLICATIONS

Lieberman et al., Pharmaceutical Dosage Forms: Tablets, vol. 2, 2$^{nd}$ edition, Marcel Dekker, Inc., New York (1990)—Abstract Only.

* cited by examiner

*Primary Examiner*—S. Tran
(74) *Attorney, Agent, or Firm*—Chalin A. Smith; Smith Patent Consulting, LLC

(57) ABSTRACT

The present invention relates to an adsorbate, comprising an adsorbent and bicalutamide adsorbed on said adsorbent, a process for preparing same, and a pharmaceutical composition thereof.

12 Claims, 5 Drawing Sheets

BICALUTAMIDE-ADSORBATES, PROCESS FOR PREPARING SAME, AND PHARMACEUTICAL COMPOSITIONS THEREOF

FIELD OF INVENTION

The present invention relates to an adsorbate, comprising an adsorbent and bicalutamide adsorbed on said adsorbent, a process for preparing the same, and a pharmaceutical composition thereof.

BACKGROUND OF THE INVENTION

The medicinal substance known by the INN bicalutamide is also known as N-[4'-cyano-3'-trifluoromethyl-phenyl]-3-[4"-fluorophenylsulfonyl]-2-hydroxy-2-methyl-propionamide.

Racemic bicalutamide can be prepared by known processes, e.g. the ones described or referred to in U.S. Ser. No. 10/498,862 (corresponding to WO 03/097590 A1).

Bicalutamide and related acylanilides are compounds exhibiting antiandrogenic activity. A racemic bicalutamide containing drug for the treatment of prostate cancer is marketed under the trade name CASODEX® (Astra Zeneca).

Bicalutamide is sparingly soluble in water and aqueous buffers at various pH values. Furthermore, the speed of being dissolved appears to depend on the particle size of the drug. WO 2004/100944 A1 and U.S. Pat. No. 6,861,557 B2 therefore describe the use of micronized bicalutamide in pharmaceutical preparations in order to enhance the speed of dissolution and, hence, the bioavailability of the drug. Moreover, bicalutamide is reported to crystallize in two different polymorphic forms, called I and II, or to be amorphous (cf. WO 2004/100944 A1). In addition to particle size, the morphology, or changes of the morphology during storage, may affect the drug dissolution profile.

The principle of micronizing bicalutamide for said pharmaceutical preparations is the application of conventional micronization techniques (various types of mills, sieving procedures, etc.), as disclosed in Liebermann et. al., Pharmaceutical Dosage Forms: Tablets, Vol. 2, 2nd ed., Marcel Dekker, Inc. New York, 1990. However, due to the high toxicity of bicalutamide, all kinds of conventional micronization and sieving procedures require severe protective measures. Particularly potential dust development and cleaning procedures are of high risk. In addition, production of pharmaceutical dosage forms from micronized material is very costly since it involves granulation, drying, and sieving steps. Overall, the micronization and sieving steps, as well as the manufacturing of pharmaceuticals from micronized bicalutamide, may lead to significant losses of this expensive and toxic material.

OBJECTS AND SUMMARY OF THE INVENTION

The present invention relates to the finding that pharmaceutical compositions containing bicalutamide and exhibiting good drug release properties/profiles can be obtained from certain adsorbates. Thus, according to one object, the present invention is directed to an adsorbate, comprising an adsorbent and bicalutamide adsorbed on said adsorbent.

According to another object, the present invention is directed to a process for preparing an adsorbate, said adsorbate comprising an adsorbent and bicalutamide adsorbed on said adsorbent. The process comprises the steps of providing a suspension of said adsorbent in a solution of bicalutamide and recovering said adsorbate from said suspension.

According to another object, the present invention provides an adsorbate, which can be obtained by the above process.

According to another object, the present invention provides a pharmaceutical composition, comprising an adsorbate according to this invention and optionally pharmaceutically acceptable excipients and/or adjuvants.

According to another object, the present invention provides a process of treating an androgen disorder, comprising administering an effective amount of the pharmaceutical composition of the present invention to a patient in need of such treatment.

DETAILED DESCRIPTION OF THE INVENTION

Figure 1:
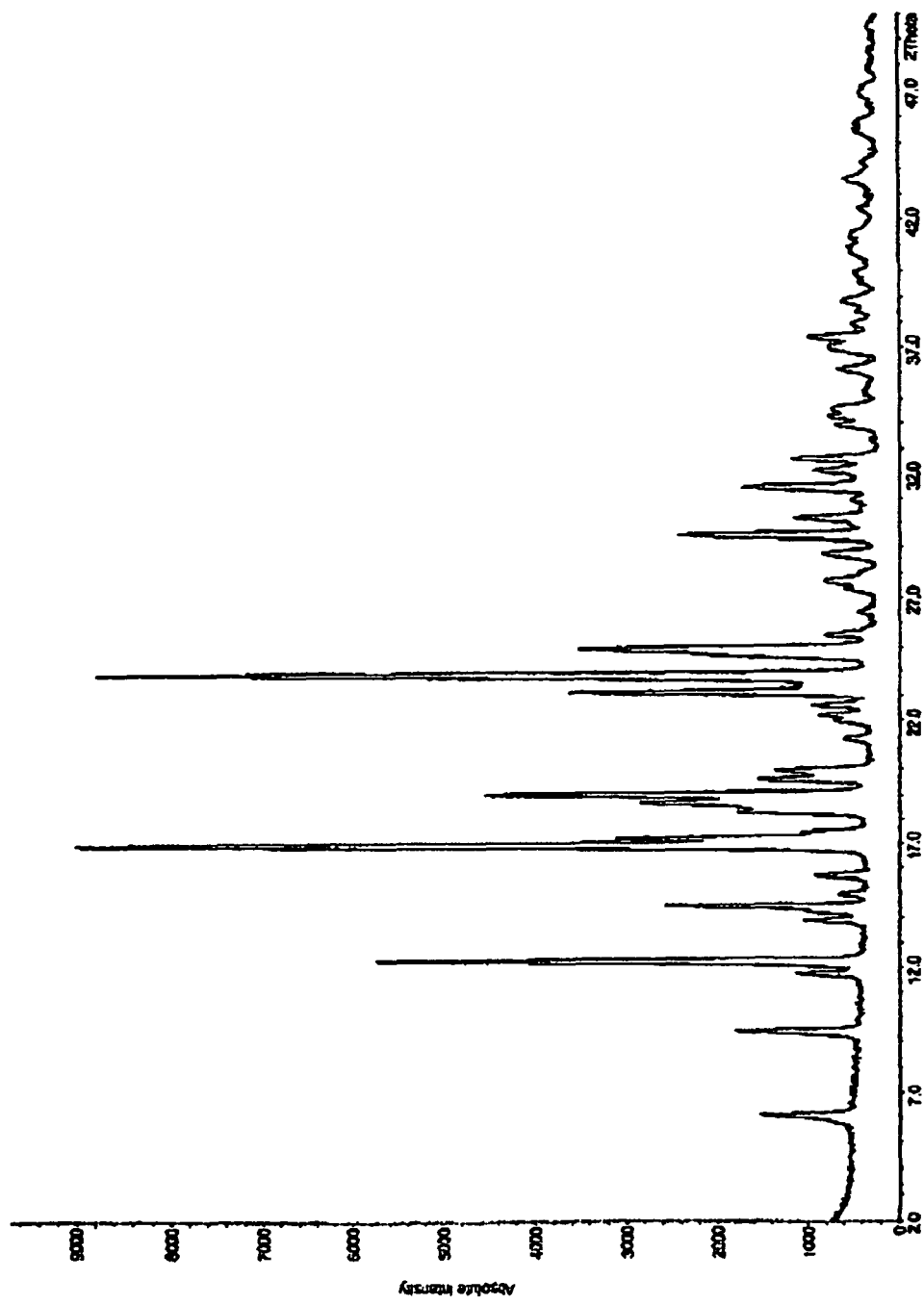
FIG. 1 shows a powder x-ray diffraction pattern of bicalutamide.

The present invention provides an adsorbate, comprising an adsorbent and bicalutamide adsorbed on said adsorbent. Surprisingly, it has been found that in such adsorbents bicalutamide is present in a morphologically defined and stable form. Moreover, from pharmaceutical preparations prepared with these adsorbates the sparingly soluble active compound, bicalutamide, is rapidly released. Additionally, the adsorbate can be prepared in a simple and economical process avoiding the disadvantages described above, in particular avoiding the need of micronization.

In the adsorbates of the present invention the adsorbent may preferably be selected from cellulose, cellulose derivatives, polyols, sugars, sugar alcohols and other sugar derivatives, starches, pre-gelatinized starches, starch derivatives, modified starches, dextrins, maltodextrins, polydextroses, dextroses, inorganic excipients, and mixtures thereof. As inorganic excipients calcium carbonate, calcium phosphate, calcium sulfate, and mixtures thereof may be exemplified. Preferred adsorbents are microcrystalline cellulose, lactose, mannitol, starch, pre-gelatinized starch, and calcium phosphate, particularly preferred in qualities usually applied for the manufacturing of tablets by direct compression.

In an advantageous embodiment of the present invention the adsorbent is selected from direct compressable excipients known to the skilled person. In this case tablets can be prepared from the adsorbate of the present invention by direct compression. As direct compressable excipients sugars, polyols, starch products, and mixtures thereof can be exemplified.

In the adsorbate of the present invention the weight ratio of bicalutamide to adsorbent is preferably in the range of from 1:0.1 to 1:10, more preferably in the range of from 1:0.5 to 1:5, and most preferred about 0.8:1.0.

The present invention further provides a process for preparing an adsorbate which comprises an adsorbent and bicalutamide adsorbed on said adsorbent. This process comprises the steps of providing a suspension of said adsorbent in a solution of bicalutamide and recovering said adsorbate from said suspension.

In the process of the present invention the solution of bicalutamide can be prepared with a solvent in which the bicalutamide is soluble while the adsorbent should be not soluble or only sparingly soluble in this solvent. Preferably at least one organic solvent is used as solvent to prepare the solution of bicalutamide. More preferably, the organic solvent should have a total water content of no more than about 15% by volume, in particular of no more than about 5% by volume.

As organic solvents suitable in the process of the present invention lower alkanols, such as alkanols having 1 to 4 carbon atoms, ethers, esters, aliphatic ketones, and mixtures thereof can be exemplified. Preferably the organic solvent is selected from methanol, ethanol, isopropanol, n-propanol, acetone, ethyl acetate, methyl ethyl ketone, methyl tert-butyl ether (MTBE), acetonitrile, tetrahydrofurane (THF), and mixtures thereof.

In the process of the present invention the suspension of said adsorbent in a solution of bicalutamide can be prepared by either suspending said adsorbent in said solution or dissolving bicalutamide in a suspension of said adsorbent. In one embodiment of the invention, the solution of bicalutamide is prepared by dissolving the bicalutamide in the solvent to obtain said solution and then the adsorbent is suspended in said solution.

In the process of the present invention the adsorbate can be recovered from the suspension by any suitable means, such as removal of the solvent. Removal of the solvent by for example drying can be promoted by increasing the temperature and/or by applying a vacuum. Equally well, freeze-drying ran be used. The solvent can be recovered by working in a closed system and re-used for a subsequent process.

With the process according to the present invention, adsorbates are obtained which are defined and stable with respect to the morphology of the bicalutamide. Moreover, the adsorbates are characterized by a rapid release of the active ingredient in aqueous solutions and aqueous buffer solutions. According to the invention, a process has been found which, starting from a solution of bicalutamide, leads to adsorbates that are suitable for immediate further processing, without any micronization of the active compound required.

Figure 2:
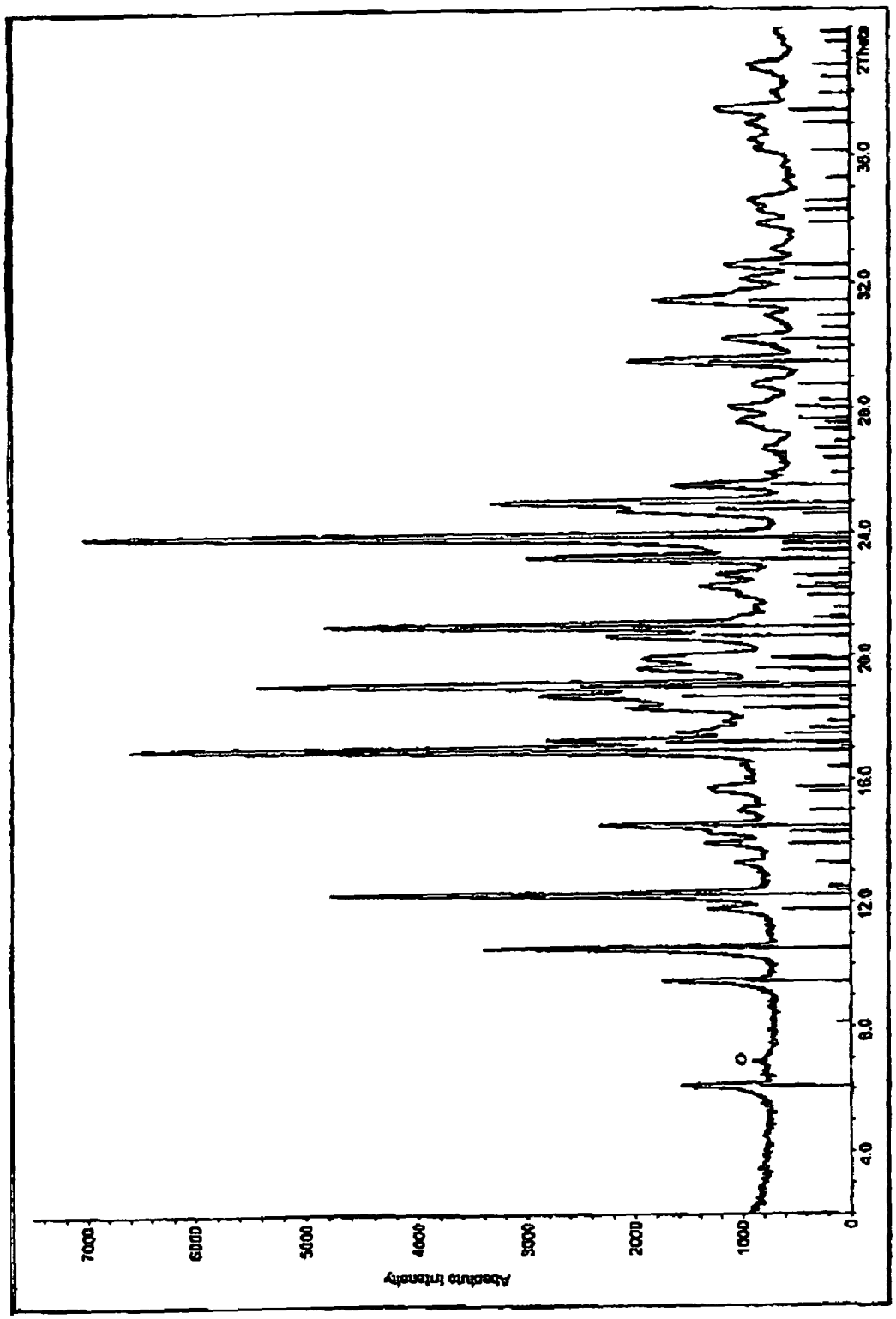
FIG. 2 shows a powder x-ray diffraction pattern of the adsorbate prepared according to Example 2.
Figure 3:
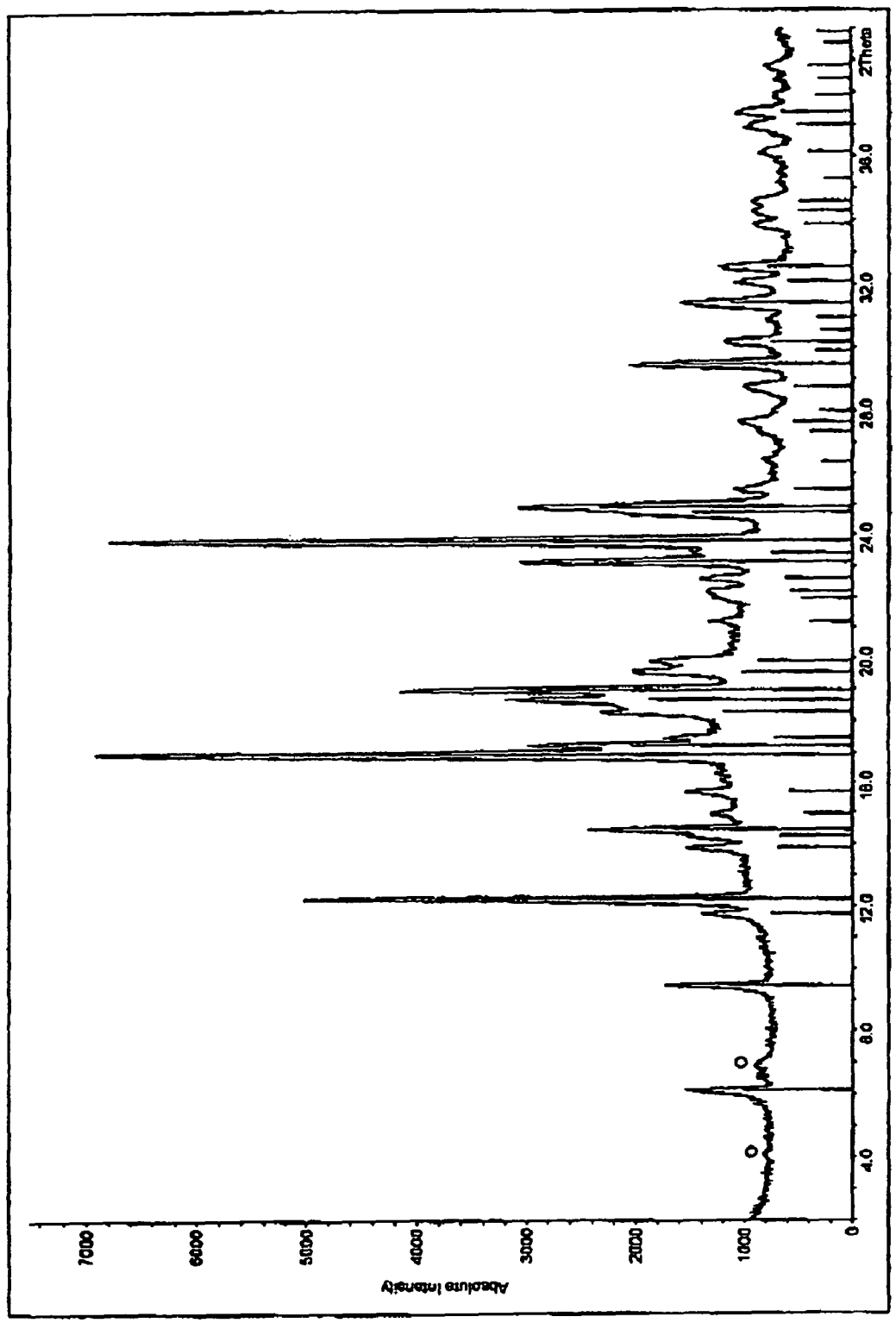
FIG. 3 shows a powder x-ray diffraction pattern of the adsorbate prepared according to Example 3.
Figure 4:
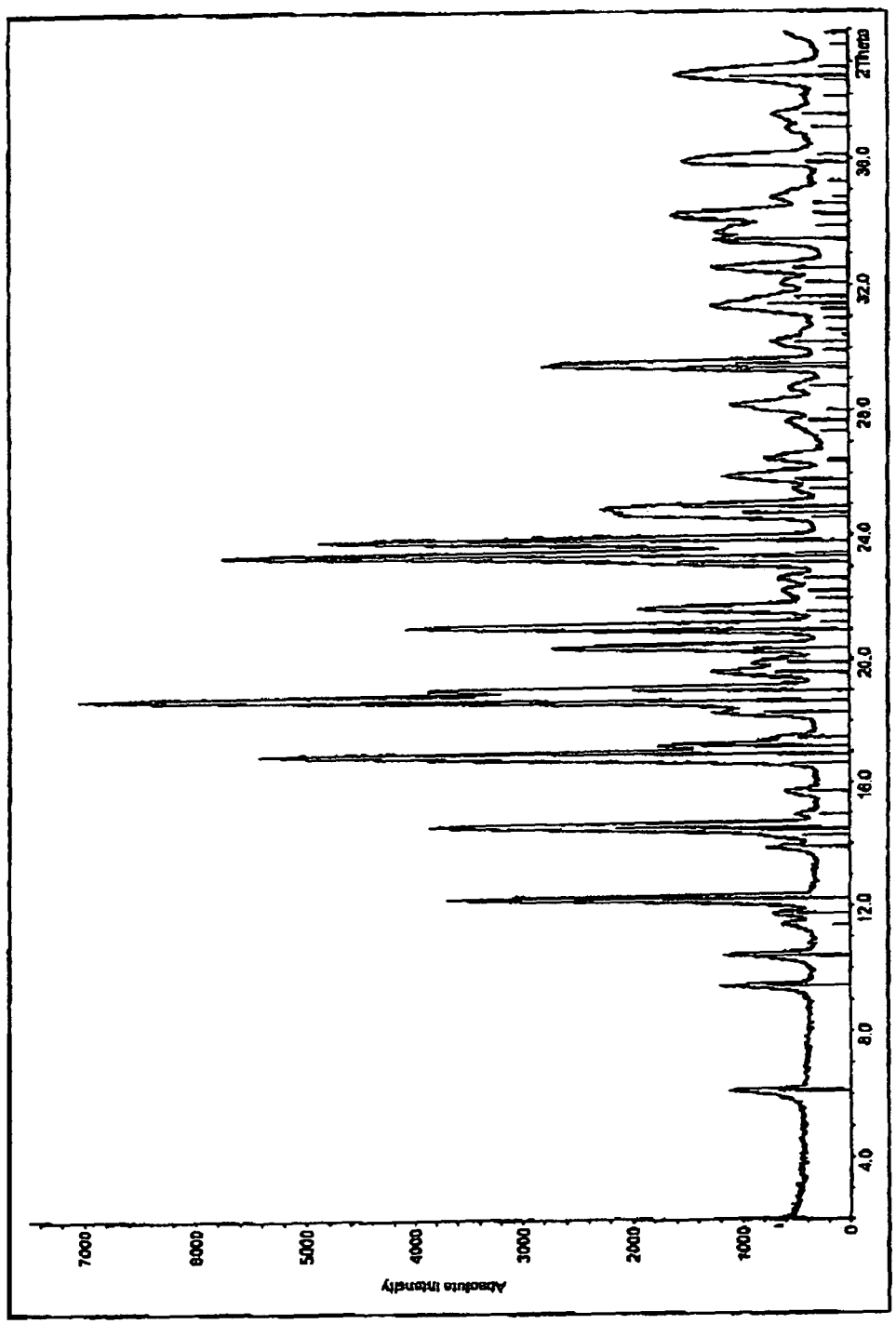
FIG. 4 shows a powder x-ray diffraction pattern of the adsorbate prepared according to Example 4.

FIGS. 1 to 4 illustrate that in the adsorbates of the present invention, which can be obtained by the above process, bicalutamide is present in a morphologically defined form. FIG. 1 shows a powder x-ray diffraction pattern of bicalutamide while FIGS. 2 to 4 show the powder x-ray diffraction patterns of adsorbates of the present invention. From these figures it is evident that the adsorbates contain bicalutamide in a morphologically defined form. The rapid release of bicalutamide from tablets prepared by direct compression of adsorbates of the present invention in admixture with excipients is demonstrated by the dissolution profiles shown in FIG. 5 in comparison with the dissolution profile of CASODEX® 50 mg tablets.

The present invention further relates to a pharmaceutical composition, comprising an adsorbate as described above and optionally pharmaceutically acceptable excipients and/or adjuvants.

All common pharmaceutical excipients can be used to prepare the pharmaceutical preparations. As fillers and/or binders, for example, celluloses and cellulose derivates (for instance microcrystalline cellulose, native cellulose, hydroxypropyl cellulose, hydroxypropyl methyl cellulose, methyl cellulose), sugars (for instance lactose, fructose, saccharose, glucose, maltose), sugar alcohols (for instance lactitol, mannitol, sorbitol, xylitol), inorganic fillers (for instance calcium phosphates and calcium sulfates), and starches (for instance corn starch, potato starch, wheat starch, dextrins, pregelatinized starches) can be used. Furthermore, all other excipients known to those skilled in the art from their general galenic knowledge, such as lubricants, disintegration aids, wetting agents, agents to improve the flow behaviour, alkaline additives, stabilizers, as well as flavours, pigments, and dyes, can be used to prepare the pharmaceutical preparations according to the invention.

In the total mixture of the pharmaceutical preparation of the present invention binders may for example be present in an amount of from 0 to 20% by weight, fillers and adjuvants may for example be present in the total mixture in an amount of from 20 to 99% by weight, preferably 50 to 99% by weight.

The pharmaceutical composition of the present invention may be a unit dosage form, such as capsules, tablets, granules, and pellets. Preferably the composition is in the form of a tablet, which is prepared by direct compression.

Where necessary for specific applications, the pharmaceutical preparation of the present invention can be further provided with a common film coating, for instance for controlled release and/or taste masking and/or improved stability. Suitable coatings are known to those skilled in the art.

Surprisingly, from the pharmaceutical preparation of the present invention the active ingredient, bicalutamide, is released essentially similar to marketed tablet formulations. Preferably, the active ingredient is released such that the pharmaceutical composition of the present invention exhibits a dissolution profile in vitro such that at 15 minutes at least about 50% of the bicalutamide has been released. More preferably, the pharmaceutical composition exhibits a dissolution profile in vitro such that at 30 minutes at least about 75% of the bicalutamide has been released.

Finally, the present invention provides a process of treating an androgen disorder, comprising administering an effective amount of the pharmaceutical composition described above to a patient in need of such treatment.

The following examples are provided to further illustrate the adsorbates, pharmaceutical compositions, and processes of the present invention. These examples are illustrative only and are not intended to limit the scope of invention in any way.

EXAMPLES

In the examples the following methods of analysis are used:

1. Release of active ingredient (dissolution test) according to USP, method II, 900 ml water, 2.0% sodium lauryl sulfate, 37° C. 75 rpm, UV detection (270 nm).
2. The powder x-ray diffraction patterns were recorded as follows:

| | |
|---|---|
| Instrument: | STADI P transmission diffractometer |
| | Cu Kα$_1$ radiation (I = 1.54056 Å), U = 40 kV, I = 30 mA |
| | Secondary beam monochromator (flat, graphite) |
| Detector: | Scintillation counter |
| Aperture: | 2 × 8 mm, 0.7 mm, 0.35 mm |
| Linear PSD: | 2Θ = 2° to 35°. 5 s/0.04° in steps |
| Sample: | Powder, reflection mode |

Example 1

Preparation of Bicalutamide Tablets, Formula 1

To a solution of bicalutamide in atone (0.08 g/ml), the absorbent lactose is added (0.10 g/ml) and homogenously suspended. The solvent is removed, using a rotary evaporator, under vacuum and gentle heating. The free flowing adsorbate is finally dried at 35° C. for 20 minutes, to remove residual solvent. The adsorbate is mixed with excipients, according to the following formulation;

| | |
|---|---|
| Bicalutamide-lactose-adsorbate | 112.5 mg |
| Excipients | 20 mg |
| (Sodium starch glycolate; povidone; microcrystalline cellulose; magnesium stearate) | |

Suitable amounts of excipients are known to those skilled in the art from their general knowledge, and can be taken from standard references for tablet formulation.

The mixture is directly compressed to tablets, having the following properties:

| | |
|---|---|
| Compressibility and flowability: | good |
| Mean hardness: | 68 N |
| Dissolution rate: | 51% after 15 min. |

The tablets thus obtained may be coated if required.

Example 2

Preparation of Bicalutamide Tablets, Formula 2

To a solution of bicalutamide in acetone (0.08 g/ml), the absorbent, a pre-mix of 38% by weight of lactose and 62% by weight of starch is added (0.10 g/ml) and homogenously suspended. The solvent is removed, using a rotary evaporator, under vacuum and gentle heating. The free flowing adsorbate is finally dried at 35° C. for 20 minutes, to remove residual solvent.

The x-ray diffraction pattern of the adsorbate is shown in FIG. 2.

The adsorbate is mixed with excipients, according to the following formulation:

| | |
|---|---|
| Bicalutamide-lactose/starch-adsorbate | 112.5 mg |
| Excipients (see Example 1) | 20 mg |

Figure 5:
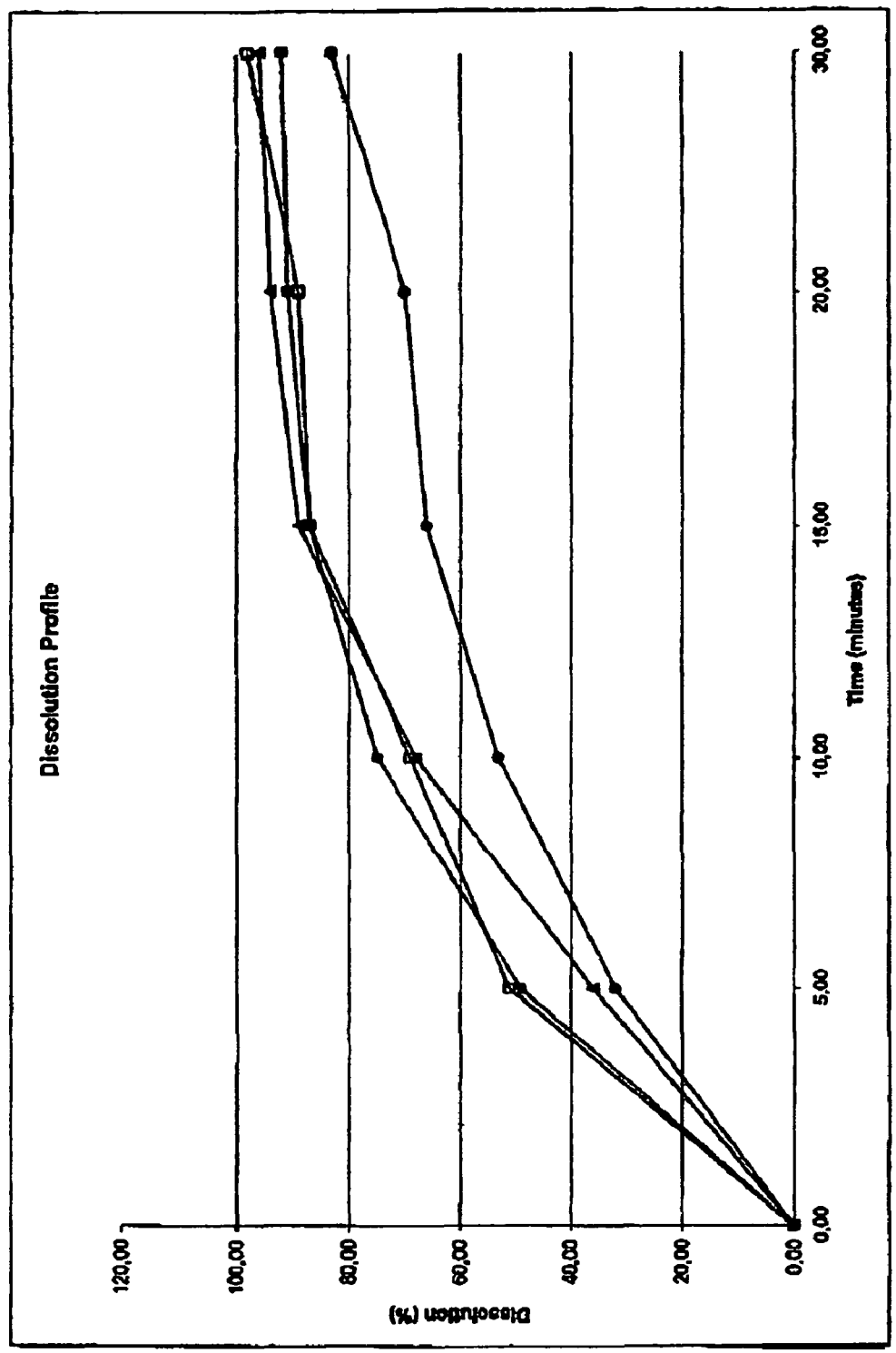
FIG. 5 shows the dissolution profile of CASODEX® 50 mg tablets, Batch No. 26006 (▲), in comparison with the dissolution profiles of tablets prepared from the adsorbates according to Examples 2 (●), 3 (+), and 5 (□), respectively.

The mixture is directly compressed to tablets, having the following properties:

| | |
|---|---|
| Compressibility and flowability: | good |
| Mean hardness: | 54 N |
| Dissolution rate: | The dissolution profile is shown in FIG. 5 |

The tablets thus obtained may be coated if required.

Example 3

Preparation of Bicalutamide Tablets, Formula 3

To a solution of bicalutamide in acetone (0.08 g/ml), the absorbent pre-gelatinized starch is added (0.10 g/ml) and homogenously suspended. The solvent is removed, using a rotary evaporator, under vacuum and gentle heating. The free flowing adsorbate is finally dried at 35° C. for 20 minutes, to remove residual solvent.

The x-ray diffraction pattern of the adsorbate is shown in FIG. 3.

The adsorbate is mixed with excipients, according to the following formulation:

| | |
|---|---|
| Bicalutamide-pre-gelatinized starch-adsorbate | 112.5 mg |
| Excipients (see Example 1) | 20 mg |

The mixture is directly compressed to tablets, having the following properties:

| | |
|---|---|
| Compressibility and flowability: | good |
| Mean hardness: | 61 N |
| Dissolution rate: | The dissolution profile is shown in FIG. 5 |

The tablets thus obtained may be coated if required.

Example 4

Preparation of Bicalutamide Tablets, Formula 4

To a solution of bicalutamide in acetone (0.089/ml), the absorbent mannitol is added (0.10 g/ml), and homogenously suspended. The solvent is removed, using a rotary evaporator under vacuum and gentle heating. The free flowing adsorbate is finally dried at 35° C. for 20 minutes, to remove residual solvent.

The x-ray diffraction pattern of the adsorbate is shown in FIG. 4.

The adsorbate is mixed with excipients, according to the following formulation:

| | |
|---|---|
| Bicalutamide-mannitol-adsorbate | 112.5 mg |
| Excipients (see Example 1) | 20 mg |

The mixture is directly compressed to tablets, having the following properties:

| | |
|---|---|
| Compressibility and flowability: | good |
| Mean hardness: | 71 N |
| Dissolution rate: | 50% after 15 min. |

The tablets thus obtained may be coated if required.

Example 5

Preparation of Bicalutamide Tablets, Formula 5

To a solution of bicalutamide in acetonitrile (0.08 g/ml), the absorbent pre-gelatinized starch is added (0.10 g/ml), and homogenously suspended. The solvent is removed using a rotary evaporator under vacuum and gentle heating. The free flowing adsorbate is finally dried at 35° C. for 20 minutes, to remove residual solvent. The adsorbate is mixed with excipients, according to the following formulation:

| | |
|---|---|
| Bicalutamide- pre-gelatinized starch-adsorbate | 112.5 mg |
| Excipients (see Example 1) | 20 mg |

The mixture is directly compressed to tablets, having the following properties:

| | |
|---|---|
| Compressibility and flowability: | good |
| Mean hardness: | 64 N |
| Dissolution rate: | The dissolution profile is shown in FIG. 5 |

The tablets thus obtained may be coated if required.

The invention claimed is:

1. A process for preparing an adsorbate, said adsorbate comprising an adsorbent and bicalutamide adsorbed on said adsorbent, wherein the weight ratio of bicalutamide to adsorbent is in the range of from 1:0.1 to 1:10, which process comprises the steps of:
   a) dissolving bicalutamide in a solvent to obtain a solution of bicalutamide,
   b) suspending the adsorbent in the bicalutamide solution so as to yield a suspension of said adsorbent in a solution of bicalutamide and
   c) recovering said adsorbate from said suspension.

2. The process according to claim 1, wherein the adsorbent is selected from the group consisting of cellulose, cellulose derivatives, polyols, sugars, sugar alcohols and other sugar derivatives, starches, pre-gelatinized starches, starch derivatives, modified starches, dextrins, maltodextrins, polydextroses, dextroses, inorganic excipients, and mixtures thereof.

3. The process according to claim 2, wherein the inorganic excipient is selected from the group consisting of calcium carbonate, calcium phosphates, calcium sulfate, and mixtures thereof.

4. The process according to claim 1, wherein the adsorbent is selected from the group consisting of direct compressable excipients.

5. The process according to claim 4, wherein the direct compressable excipient is selected from the group consisting of sugars, polyols, starch products, and mixtures thereof.

6. The process according to claim 1, wherein the weight ratio of bicalutamide to adsorbent is in the range of from 1:0.5 to 1:5.

7. The process according to claim 1, wherein said solution of bicalutamide is prepared in at least one organic solvent.

8. The process according to claim 7, wherein the organic solvent has a total water content of no more than about 15% by volume.

9. The process according to claim 8, wherein the organic solvent has a total water content of no more than about 5% by volume.

10. The process according to claim 7, wherein the organic solvent is selected from the group consisting of lower alkanols, ethers, esters, aliphatic ketones, and mixtures thereof.

11. The process according to claim 10, wherein the organic solvent is selected from the group consisting of methanol, ethanol, isopropanol, n-propanol, acetone, ethyl acetate, methyl ethyl ketone, methyl tert-butyl ether, acetonitrile, tetrahydrofurane, and mixtures thereof.

12. A process of treating an androgen disorder, comprising administering an effective amount of the pharmaceutical composition comprising an adsorbate obtained by the process according to claim 1 optionally formulated with pharmaceutically acceptable excipient and/or adjuvants to a patient in need of such treatment.

* * * * *